United States Patent [19]

Kondo et al.

[11] Patent Number: 5,104,794
[45] Date of Patent: Apr. 14, 1992

[54] QUANTITATIVE DETERMINATION OF BILIRUBIN AND A REAGENT THEREFOR

[75] Inventors: Hitoshi Kondo, Uji; Kazuhiro Matsui, Tsuruga; Hiroshi Suzuki, Yachiyo, all of Japan

[73] Assignees: Unitika Ltd., Hyogo; Iatron Laboratories, Inc., Tokyo, both of Japan

[21] Appl. No.: 492,572

[22] Filed: Mar. 13, 1990

[30] Foreign Application Priority Data

Mar. 13, 1989 [JP] Japan .................................. 1-60323

[51] Int. Cl.$^5$ ...................... C12Q 1/26; G01N 33/72
[52] U.S. Cl. ........................................ 435/25; 435/4; 435/18; 435/28; 436/97; 436/903
[58] Field of Search .................... 435/4, 18, 25, 28; 436/97, 903, 175

[56] References Cited

U.S. PATENT DOCUMENTS

| | | | |
|---|---|---|---|
| 4,211,844 | 7/1980 | Wu | 435/25 |
| 4,554,249 | 11/1985 | Kosaka et al. | 435/97 X |
| 4,571,383 | 2/1986 | Takayama et al. | 435/4 X |
| 4,600,689 | 7/1986 | Matsui et al. | 435/25 |
| 4,701,411 | 10/1987 | Wu | 435/25 |
| 4,746,606 | 5/1988 | Wu et al. | 435/25 |
| 4,770,997 | 9/1988 | Yoshino et al. | 435/25 |
| 4,820,416 | 4/1989 | Chang et al. | 435/25 X |
| 4,895,799 | 1/1990 | Kruse-Müller et al. | 435/25 X |
| 4,937,186 | 6/1990 | Siddigi et al. | 435/25 X |
| 4,985,360 | 1/1991 | Takahashi et al. | 435/25 X |

*Primary Examiner*—Robert J. Hill, Jr.
*Attorney, Agent, or Firm*—Wenderoth, Lind & Ponack

[57] ABSTRACT

Disclosed is a process for measuring an amount of all bilirubins in a specimen, comprising deconjugating conjugated bilirubins with a reagent comprising an enzyme capable of deconjugation to form the unconjugated bilirubin, and determining an amount of the unconjugated bilirubin in the specimen, and a reagent therefor. The present invention also provides a process for measuring an amount of the unconjugated bilirubin in a specimen, comprising oxidizing and eliminating conjugated bilirubins in the specimen with an oxidizing agent capable of oxidizing bilirubins, in the presence of a metal ion forming a complex with the bilirubins and a surfactant at pH 6.5 or less, and determining an amount of the unconjugated bilirubin in the specimen, and a reagent therefor.

26 Claims, 3 Drawing Sheets

CONCENTRATION OF THE UNCONJUGATED BILIRUBIN IN STANDARD SERUM (md/dℓ)

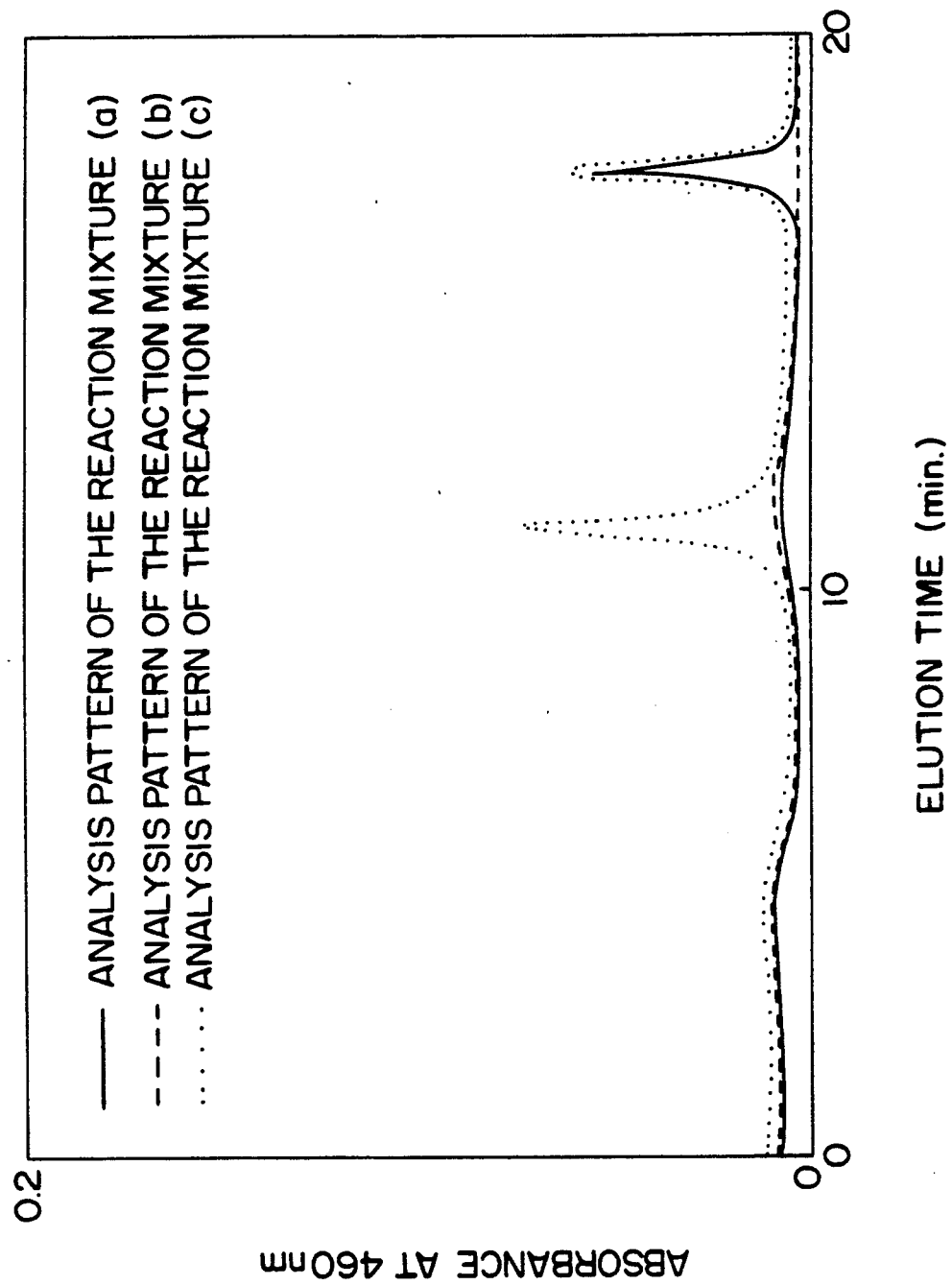

QUANTITATIVE DETERMINATION OF BILIRUBIN AND A REAGENT THEREFOR

FIELD OF THE INVENTION

The present invention relates to a process for measuring an amount of bilirubins in body fluids and a reagent therefor.

BACKGROUND OF THE INVENTION

Bilirubins are yellow dyes which belong to tetrapyrroles and are present as unconjugated bilirubin and conjugated bilirubins in body fluids. Conjugated bilirubins are those in which sugars (e.g. glucuronic acid) are attached to propionic acid groups of the bilirubins, while the unconjugated bilirubin is bilirubin which is not chemically modified.

In case of a disease like hemolytic anemia or hemolytic jaundice, an amount of the unconjugated bilirubin increases. In case of a disease like obstructive jaundice an amount of conjugated bilirubins increase. Accordingly, the separation and quantitative determination of bilirubins are very important in clinical diagnosis.

There have been proposed many methods for the separation and quantitative determination of bilirubins, such as a method using a diazo reagent, a method using high performance liquid chromatography (HPLC), a method using an oxidizing enzyme such as bilirubin oxidase and the like.

The method using a diazo reagent has many variations due to a sort of a diazotization reaction accelerator and a difference of a quantitative measurement of produced azobilirubins. Typical examples of the methods are a reagent of Malloy & Evelyn et al. (Journal of Biological Chemistry, Volume 119, p 481, 1937) and the like.

The method using high performance liquid chromatography (HPLC) has some variations, such as a Lauff et al. method wherein various bilirubins are eluted and analyzed by the gradient of a phosphate buffer solution and isopropanol, using a reversed phase HPLC column (Journal of Chromatography, Volume 226, p 391, 1981) and the like.

The method using an oxidizing enzyme is a method wherein the bilirubins are oxidized by the oxidizing enzyme to eliminate the absorption of around 450 nm of the bilirubins, whereby an amount of the bilirubins is calculated from the absorption change between before and after the reaction. In this method, the specificity of the oxidation onto the bilirubins can be varied by changing reaction conditions. Reagents for this method include a reagent which contains bilirubin oxidase (Clinical Chemistry, Volume 20, p 783, 1974); a reagent which contains another oxidizing agent, such as laccase, tyrosinase, ascorbic acid oxidase and the like (Japanese Kokai Publication (unexamined) 17999/1984); a reagent for a quantitative determination of all bilirubins, which employs a nonionic surfactant (e.g. cholic acid etc.) or an aromatic carboxylic acid as a reaction accelerator (Japanese Kokai Publication (unexamined) 249060/1984 etc.); and a reagent for a quantitative determination of conjugated bilirubins wherein bilirubin oxidase is only acted on conjugated bilirubins by controlling pH, a buffer solution and a surfactant. Examples of the reagents for conjugated bilirubins are a reagent whereby bilirubin oxidase is used in a buffer solution of pH 9 to 11 (Japanese Kokai Publication (unexamined) 58999/1987), a reagent whereby bilirubin oxidase is used in a buffer solution of pH 5 to 6 which contains an anionic surfactant (Japanese Kokai Publication (unexamined) 152955/1985), a reagent whereby bilirubin oxidase is used in a buffer solution of pH 3.5 to 4.5 (Japanese Kokoku Publication (examined) 44000/1986) and the like. Also, Japanese Kokai Publication (unexamined) 154162/1985 discloses a reagent for the unconjugated bilirubins whereby a ratio of bilirubin in a specimen and bilirubin oxidase is limited within a specified range in a buffer solution of pH 8.0 which contains an anionic surfactant.

In the method using a diazo reagent, all bilirubins and conjugated bilirubins are separately determined by whether a reaction accelerator of the diazotization reaction is contained in the reagent or not. The separation ability, however, is insufficient in practical use and more insufficient for a specimen which does not contain albumin or which contains chemicals, such as salicylic acid. It is also a problem in this method that, since the azobilirubins produced by the diazotization of conjugated bilirubins or the unconjugated bilirubin respectively have different spectrochemical properties, inaccuracy occurs in measured results. Further, ditaurobilirubin which is used as a standard material of conjugated bilirubins is different from conjugated bilirubins in reactivity and spectrochemical properties after diazotization.

The method using HPLC has sufficient selectivity, but requires an expensive and unique apparatus. It also takes a long period of time to measure. The number of specimens to be measured is also limited.

The method using another oxidizing enzyme has a problem in that no adequate standard material is present, the situation of which is similar to the method using a diazo reagent. Since ditaurobilirubin or unconjugated bilirubins are different from conjugated bilirubins in body fluids in spectrochemical properties (e.g. absorptivity coefficient, peak absorption wavelength etc.) or reactivity with a reagent, inaccuracy may occur in measured results. Thus, errors arise when bilirubins in body fluids are separately determined using one standard material. It is also proposed that a combination of ditaurobilirubin and the unconjugated bilirubin is used as a standard material, but a combination ratio has to be selected according to body fluids, and thus its preparation is difficult. The reagents for determining conjugated bilirubins are formulated with the premise that proteins, such as albumin, are present in the specimen. It therefore is difficult for them to precisely measure a specimen which contains a high ratio of bilirubins which are free from proteins, such as serum of a new born baby or serum containing salicylic acid.

Further, Japanese Patent Publication (examined) 44000/1986 discloses a reagent for the quantitative determination of conjugated bilirubin, of which a pH range, however, is disadvantageous for bilirubin oxidase in view of stability and activity.

The method measuring the unconjugated bilirubin, as described in Japanese Kokai Publication (unexamined) 154162/1985, is not suitable for a specimen which contains the unconjugated bilirubin in an unknown concentration, because an amount of bilirubin oxidase should be controlled by an amount of the unconjugated bilirubin. Also, since the reagent used for this method functions not only on the unconjugated bilirubin but on some of conjugated bilirubins, the result of this method is inaccurate.

SUMMARY OF THE INVENTION

The present invention provides a process for measuring an amount of all bilirubins in a specimen, comprising deconjugating conjugated bilirubins with a reagent comprising an enzyme capable of deconjugation to form the unconjugated bilirubin, and determining an amount of the unconjugated bilirubin in the specimen.

The present invention also provides a reagent for measuring an amount of all bilirubins comprising an enzyme capable of deconjugation, and an oxidizing agent capable of oxidizing bilirubins or a diazotating agent.

The present invention further provides a process for measuring an amount of the unconjugated bilirubin in a specimen, comprising oxidizing and eliminating conjugated bilirubins in the specimen with an oxidizing agent capable of oxidizing bilirubins, in the presence of a metal ion forming a complex with bilirubins and a surfactant at pH 6.5 or less, and determining an amount of the unconjugated bilirubin in the specimen.

Also, the present invention provides a reagent for measuring an amount of the unconjugated bilirubin in a specimen, comprising a first reagent comprising an oxidizing agent capable of oxidizing bilirubins, a metal ion forming a complex with bilirubins, a surfactant and a buffer solution of pH 6.5 or less, and a second reagent comprising at least one component selected from the group consisting of a chelating agent, a buffer solution of pH 6.5 or more and a surfactant.

DETAILED DESCRIPTION OF THE INVENTION

Measurement of all bilirubins

The reagent for measuring an amount of all bilirubins of the present invention is constituted from two reagents. The first reagent mainly contains an enzyme capable of deconjugating conjugated bilirubins to the unconjugated bilirubin and the second reagent mainly contains an oxidizing agent to measure an amount of the unconjugated bilirubin produced by the function of the ingredients of the first reagent.

The enzyme of the first reagent includes a sugar ester hydrolase, such as glucuronidase, glucosidase, galactosidase etc,; sulfatase; and a mixture thereof. In case where the specimen is body fluids of humans, preferred is glucuronidase which is not combined with the other enzymes. The enzyme may be derived from any animals, plants or microorganisms, for example, glucuronidase which is derived from bovine livers, snails or *Escherichia coli*; glucosidase which is derived from yeasts or almonds; galactosidase which is derived from *Escherichia coli*, and sulfatase which is derived from snails. The enzyme can be employed in a concentration of 0.01 to 100 units/ml, preferably 0.05 to 50 units/ml. Concentrations of less than 0.01 units/ml take a long time to complete deconjugating reactions. Concentrations of more than 100 units/ml make the reagent expensive and delay the deconjugating reactions due to a high protein concentration. Also, conjugated bilirubins may be oxidized with impurities contained in the enzyme.

The oxidizing agent of the second reagent, capable of oxidizing the bilirubins, includes an enzyme capable of oxidizing bilirubins, such as bilirubin oxidase or laccase; a combination of an oxidase for producing hydrogen peroxide, such as glucose oxidase, peroxidase and a substrate thereof; a transition metal ion capable of oxidizing the bilirubins, or a salt thereof, such as copper sulfate, copper chloride, ferric sulfate and the like; and a peroxide, such as potassium persulfate, sodium perbenzoate and the like. The diazo reagent of the second reagent includes a hydrochloric acid solution containing sulfanilic acid and nitrous acid, a mixture of 2,4-dichloroaniline and sulfanilic acid and the like; or a combination thereof. A concentration of the oxidizing agent is 0.01 to 30 units/ml, preferably 0.05 to 10 units/ml for the enzyme for oxidizing bilirubins; 0.01 to 50 mM, preferably 0.05 to 30 mM for the peroxide; 0.01 to 20 mM, preferably 0.05 to 5 mM for the transition metal ion or a salt thereof; 0.05 to 5 mM, preferably 0.1 to 2 mM for the diazo reagent. If the concentration is outside the above range, it takes a long time to complete the oxidizing reactions of the unconjugated bilirubin or the deterioration of the reagent is significant. It also has a possibility to produce precipitates. The oxidizing enzyme may be derived from anything. For example, laccase can be derived from lacquer trees or microorganisms (e.g. genus Polyporus), bilirubin oxidase can be derived from microorganisms (e.g. genus Myrothecium or genus Trachyderma) or glucose oxidase can be derived from microorganisms (e.g. genus Aspergillus, etc.).

In addition to the above mentioned components, the first or second reagent may further contain a reaction promoter (e.g. an aromatic carboxylic acid), a surfactant, a buffer, a chelating agent, activating agents or salts. Examples of the aromatic carboxylic acids are p-toluenesulfonic acid, benzoic acid and the like. The aromatic carboxylic acid may be present in the reagent in a concentration of 5 to 7 mM, preferably 10 to 50 mM. If the concentration is outside the above range, it takes a long time to complete reactions or precipitates may occur. The surfactant may be anionic, nonionic, cationic or ampholytic, for example sodium dodecylsulfate, cholic acid, polyoxyethylene glycol, Triton X-100 (available from Nakarai Chemical Co., Ltd.), Tween 80 (available from Wako Pure Chemical Industries), lauryl pyridinium chloride, lauryl trimethylammonium chloride, N-lauryl myristyl-beta-aminopropionic acid, N-lauryl-beta-imino-dipropionic acid and the like. The surfactant may be present in the reagent in a concentration of 0.01 to 10% by weight, preferably 0.05 to 2% by weight. Concentrations of more than 10% by weight may produce precipitates and reduce flowability to result in making it difficult to apply to an automatic analyzer.

The buffer solution for the first reagent is preferably one which has a pH range near an optimum pH range of the enzyme capable of deconjugation, and the buffer solution for the second reagent is preferably one which has a pH range near an optimum pH range of the oxidizing agent. Examples of the buffer solutions for the first reagent are a phthalic acid-sodium hydroxide buffer (pH 5), a succinic acid-sodium hydroxide buffer (pH 5) and the like, if it employs beta-glucuronidase derived from bovine liver. Examples of the buffer solutions for the second reagent are a phosphoric acid buffer (pH 7.0), a HEPES buffer (pH 7.0) and the like, if the oxidizing agent is bilirubin oxidase. The buffer solution may be used in a concentration of 20 to 500 mM, preferably 30 to 200 mM. If it is less than 20 mM, a pH value of the reagent may change when a specimen is added to the reagent. If it is more than 500 mM, it takes a long time to react and precipitation may occur in the reagent.

The chelating agent includes a polyaminocarboxylic acid such as ethylenediaminetetraacetic acid (EDTA), or an oxycarboxylic acid such as citric acid. The chelating agent can be present in the reagent in a concentration of 0.01 to 100 mM, preferably 0.05 to 50 mM.

The fillers include polyethylene glycol, albumin, sugars and the like. Polyethylene glycol may be employed in a concentration of 0.01 to 10%, preferably 0.05 to 2%, albumin may be 0.01 to 50 mM, preferably 0.05 to 10 mM and sugars may be 1 to 100 mM, preferably 5 to 50 mM.

Salts include sodium chloride, ammonium chloride, potassium sulfate and the like. It may be employed in a concentration of 1 to 500 mM, preferably 5 to 100 mM.

The reagent for measuring an amount of all bilirubins of the present invention generally contains the unconjugated bilirubin as a standard material in a known concentration within 0.1 to 80 mg/dl, preferably 0.5 to 60 mg/dl. The unconjugated bilirubin is that which is available from Daiichi Kagaku Yakuhin Co., Ltd. or Shigma Chemical Co., Ltd., or which is obtained from gall bladder of pigs, horses and humans. The unconjugated bilirubin is used intact or in a combination with a stabilizing agent (e.g. polyethylene glycol, albumin, sugars, chelating agents, salts) or a filler. An amount of polyethylene glycol is within the range of 0.01% to 30% by weight, an amount of albumin is 0.01 to 50 mM, sugars are 1 to 300 mM, chelating agents are 0.01 to 100 mM and salts are 1 to 500 mM. A high bilirubin control standard serum which is commercially available can be employed, but it is desirable that the standard serum only contains the unconjugated bilirubin in a precise amount.

The first and second reagents and the standard material can take any forms, such as solution, or freeze dried, as long as they are solutions upon use. Their forms can be prepared by art-known methods.

According to the present invention, a preferred composition is described here.

The first reagent contains beta-glucuronidase derived from bovine liver in a concentration of 0.05 to 10 units/ml, p-toluenesulfonic acid in a concentration of 5 to 75 mM, EDTA in a concentration of 0.01 to 20 mM and a succinic acid-sodium hydroxide buffer of pH 4 to 6 in a concentration of 20 to 500 mM. The second reagent contains bilirubin oxidase in a concentration of 0.05 to 10 units/ml, p-toluenesulfonic acid in a concentration of 10 to 50 mM, EDTA in a concentration of 0.05 to 50 mM and a phosphoric acid buffer of pH 5 to 8 in a concentration of 20 to 500 mM.

The process for measuring a total amount of bilirubins may be carried out by converting conjugated bilirubins in a specimen with a reagent containing the enzyme capable of deconjugation into the unconjugated bilirubin, and directly determining by HPLC or determining the change in absorbance when the unconjugated bilirubins are treated with the oxidizing agent or diazo reagent to form oxidized or azotized unconjugated bilirubins, respectively. In the above mentioned process, since the conjugated bilirubins in the specimen are all converted into the unconjugated bilirubin, only the unconjugated bilirubin can be used as standard material.

In the process for measuring a total amount of bilirubins, the first reagent of 0.6 ml is pre-heated in a cell chamber in a spectrometer, to which a specimen of a suitable amount (e.g. serum) which contains various bilirubins is added and reacted for 1 to 10 minutes to convert all conjugated bilirubins to the unconjugated bilirubin, whereby an absorbance change at 460 nm is measured. Next, the second reagent of 0.15 ml is added thereto and reacted for 1 to 10 minutes to oxidize all the unconjugated bilirubin, whereby an absorbance at 460 nm is measured. An absorbance change (A) is then calculated from the latter absorbance and the former absorbance which is corrected in terms of a volume fraction. Separately, a standard material which contains the unconjugated bilirubin of a known concentration is measured as mentioned above to obtain an absorbance change (B). A total bilirubin content is calculated from the following formula;

$$\text{Total content (mg/dl) of bilirubins in the specimen} = \frac{A}{B} \times \text{Content (mg/dl) of the non-conjugated bilirubin in the standard material}$$

A temperature for pre-heating and reactions is preferably 25° to 37° C. and an amount of the specimen is preferably 0.005 to 0.1 ml. A wavelength for determination may be selected within the range of 400 to 480 nm. Amounts of the first and second reagents and the specimen may be varied.

If the specimen only contains conjugated bilirubins, the absorbance change corresponds to not only the amount of the conjugated bilirubins but also the amount of the all bilirubins in the specimen.

In case where the second reagent contains a diazo reagent, the determination can be carried out by producing azo dyes in place for oxidizing bilirubins. It is also possible that, after reacting the first reagent with the specimen, conjugated bilirubins produced are directly subjected to a quantitative analysis by using HPLC.

Measurement of the unconjugated bilirubin

The reagent for measuring an amount of the unconjugated bilirubin in a specimen of the present invention is also composed of two reagents. A first reagent does not act upon the unconjugated bilirubin but acts only upon conjugated bilirubins and a second reagent is for determining the unconjugated bilirubin which remains after the action of the first reagent.

The first reagent generally comprises a buffer solution of pH 6.5 or less, a surfactant, a metal ion which forms a complex with bilirubins, an oxidizing agent and the like. The second reagent generally comprises a component selected from the group consisting of a chelating agent, a buffer solution of pH 6.5 or more and a surfactant. The first reagent may further contain a salt, such as chloride and the like if necessary. Also, the second reagent may further contain the components as mentioned for the first reagent.

The buffer solution of the first reagent has a buffer capacity of pH 6.5 or less, preferably pH 2.0 to 6.0, for example a phthalic acid-sodium hydroxide buffer, a succinic acid-sodium hydroxide buffer, a 3,3-dimethylglutaric acid buffer and the like. The buffer solution may be employed in a concentration of 20 to 200 mM, preferably 30 to 100 mM. If a concentration is less than 20 mM, it may happen that a pH value is out of the specified pH range when the first reagent is mixed with the specimen. If a concentration is more than 200 mM, it is difficult to turn to a neutral pH range when the second reagent is added.

The surfactant for the first reagent can be the same one as described in the measurement of all bilirubins, but has a high solubility at pH 6.5 or less. Typical examples of the surfactant are a nonionic surfactant, such as Triton X-100, Tween 80, etc.; an anionic surfactant, such as sodium laurylbenzensulfonate, sodium taurodeoxycholate, sodium glycocholate etc.; and the like. The surfactant may be used in a concentration of 0.01 to 2.0% by weight, preferably 0.03 to 0.5% by weight. Concentrations of less than 0.01% by weight do not reach a critical micelle concentration and therefore do not protect the unconjugated bilirubin, while at concentrations of more than 2.0% by weight it requires a long time to completely oxidize conjugated bilirubins by the oxidizing agent.

The metal ion which forms a complex with bilirubins of the first reagent includes copper ion, iron ion or manganese ion. Preferred are copper ion and iron ion, because these ions do not act upon the unconjugated bilirubin at a low concentration. The ion can be introduced in the form of salts, such as chlorides, acetates, ammonium salts and the like. The ions can be present in the reagent in a concentration of 0.01 to 10 mM, preferably 0.05 to 5 mM. If the concentration is outside the above range, the unconjugated bilirubin can not be protected from the oxidizing agent in the first reagent, or precipitates may occur.

The oxidizing agent in the first reagent and its concentration are the same as described in the measurement of all bilirubins. If the oxidizing agent is copper ion, a reaction accelerator such as salts containing chloride ion, bromide ion, iodide ion, thiocyanic acid ion, cyanic acid ion and cyan ion can be added. The salt containing thiocyanic ion is preferred because it has a high accelerating ability and a low toxicity.

The first reagent may contain a halogenide (e.g. sodium chloride, sodium fluoride etc.) in order to use the oxidizing enzyme such as bilirubin oxidase in a pH range of 4.7 to 6.5 at which the enzyme is stable and active. The halogenide may be present in a concentration of 1 to 200 mM, preferably 5 to 50 mM. Preferred is a fluoride, because it can formulate the first reagent at pH 4.7 to 6.5. If a concentration is outside the above range, it takes a long time to eliminate conjugated bilirubins.

The chelating agent of the second reagent includes a polyaminocarboxylic acid, such as EDTA; an oxycarboxylic acid, such as citric acid; and the like. A concentration of the chelating agent may be 0.05 to 100 mM, preferably 0.05 to 50 mM. Concentrations outside the above range are insufficient to promote reactions after adding the second reagent.

The buffer solution of at least pH 6.5 or more of the second reagent includes a phosphoric acid buffer, a tris-hydrochloric acid buffer, a glycine-sodium hydroxide buffer and the like. A concentration of the buffer solution is 20 to 1,000 mM, preferably 50 to 500 mM. Concentrations outside the above range are insufficient to promote reactions after adding the second reagent.

The surfactant of the second reagent can be anionic, nonionic, cationic or ampholytic. It may be present in a concentration of 0.01 to 10% by weight, preferably 0.05 to 2% by weight. Concentrations outside the above range are insufficient to promote reactions after adding the second reagent.

In addition to the above mentioned components, the first or second reagent may further contain a reaction promoter (e.g. an aromatic carboxylic acid), a sugar (e.g. mannitol) and a polyol (e.g. polyethylene glycol). The above mentioned additional component may be present in the reagent in a concentration of 0.01 to 300 mM, preferably 0.05 to 100 mM. Concentrations outside the above range are insufficient to promote reactions after adding the second reagent.

The reagent for measuring an amount of the unconjugated bilirubin of the present invention generally contains the unconjugated bilirubin of a known concentration as a standard material.

According to the present invention, a preferred composition is described here.

The first reagent contains a phthalic acid-sodium hydroxide buffer of pH 4.7 to 6.0 in a concentration of 20 to 500 mM, Triton X-100 of 0.025 to 1% by weight, copper sulfate of 0.01 to 10 mM, bilirubin oxidase of 0.05 to 20 units/ml and sodium fluoride of 5 to 50 mM. The second reagent contains a pH 5.0 to 7.0 phosphoric acid buffer and EDTA of 0.1 to 50 mM. The second reagent may further contain bilirubin oxidase of 0.1 to 50 units/ml.

The process for measuring an amount of the unconjugated bilirubin may be carried out by oxidizing and eliminating conjugated bilirubins in a specimen with a reagent which contains an oxidizing agent capable of oxidizing bilirubins, a metal ion forming a complex with bilirubins, a nonionic surfactant and a pH 6.5 or less buffer solution. Then, the remaining the unconjugated bilirubin is oxidized with a reagent containing an oxidizing enzyme or a diazo reagent and a resultant change in absorbance at a specific wavelength is measured. The remaining unconjugated bilirubin may be directly determined by HPLC. The reagent for oxidizing and eliminating conjugated bilirubins includes the first reagent and the reagent which contains an oxidizing enzyme of the unconjugated bilirubin includes the second reagent. In the above process, the standard material is only the unconjugated bilirubin.

In the process for measuring the unconjugated bilirubin, the first reagent of 0.6 ml is pre-heated in a cell chamber in a spectrometer, to which a specimen of a suitable amount (e.g. serum) which contains various bilirubins is added and reacted for 1 to 10 minutes to oxidize and eliminate conjugated bilirubins, whereby an absorbance at 460 nm is measured. Next, the second reagent of 0.15 ml is added thereto and reacted for 1 to 10 minutes to oxidize all unconjugated bilirubin, whereby an absorbance at 460 nm is measured. An absorbance change (A) is then calculated from the latter absorbance and the former absorbance which is corrected in terms of a volume fraction. Separately, a standard material which contains the unconjugated bilirubin of a known concentration is measured as mentioned above to obtain an absorbance change (B). An unconjugated bilirubin content is calculated from the following formula;

$$\text{Content (mg/dl) of the unconjugated bilirubin in the specimen} = \frac{A}{B} \times \text{Content (mg/dl) of the unconjugated bilirubin in the standard material}$$

A temperature for pre-heating and reactions is preferably 25° to 37° C. and an amount of the specimen is preferably 0.005 to 0.1 ml. A wavelength for determination may be selected within the range of 400 to 480 nm. Amounts of the first and second reagents and the specimen may be varied.

In case where the second reagent contains a diazo reagent, the determination can be carried out by producing azo dyes in place for oxidizing bilirubins. It is also possible that, after reacting the first reagent and the specimen, the remaining unconjugated bilirubin is directly subjected to a quantitative analysis by using HPLC. Even if a specimen contains both the unconjugated bilirubin and conjugated bilirubins, an amount of conjugated bilirubins can be easily obtained by the present invention. That is, an amount of all bilirubins in the specimen is obtained with the reagent for all bilirubins of the present invention and then an amount of the unconjugated bilirubin is obtained with the reagent for the unconjugated bilirubin of the present invention. Accordingly, an amount of conjugated bilirubins can be obtained by (the amount of all bilirubins-the amount of the unconjugated bilirubin). Since the reagents of the present invention employ the unconjugated bilirubin as standard material, the determination according to the present invention is very precise.

BRIEF DESCRIPTION OF THE DRAWINGS

FIG. 3 is an HPLC analysis pattern which is conducted in Example 7.

EXAMPLES

The present invention is illustrated by the following Examples which, however, are not to be construed as limiting the invention to their details.

REFERENCE EXAMPLE 1

Glucuronide bilirubins, one of conjugated bilirubins, were purified from pig bile as described in Bunseki Kagaku, Volume 31, E 63 page, 1982. Glucuronide bilirubins and the unconjugated bilirubin were analyzed by modifying the Lauff et al. method (Journal of Chromatography, Volume 226, p 391, 1981. The analysis was carried out using a Lichrosorb RP-8 (particle size of 10 micrometer) chromatographic column with a gradient elution of a phosphoric acid buffer solution (pH 2.0) containing 5% methyl cellosolve and acetonitrile.

EXAMPLE 1

A reagent for measuring an amount of all bilirubins was prepared as follow.

Figure 1:
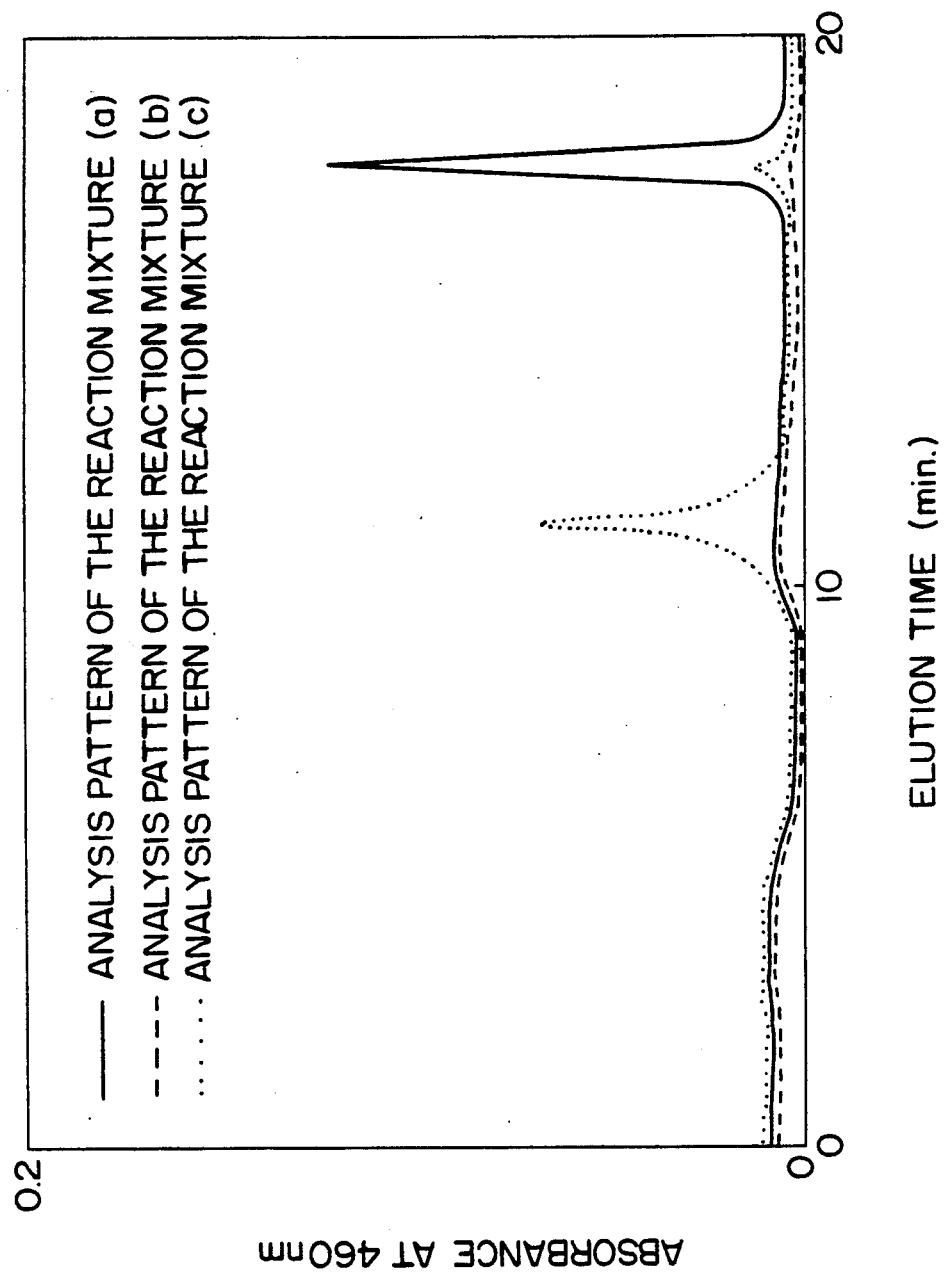
FIG. 1 is an HPLC analysis pattern of Example 1.

The first reagent was prepared from beta-glucuronidase (available from Shigma Chemical Co., Ltd. as G0251) of 0.2 units/ml, p-toluenesulfonic acid of 30 mM, EDTA of 1 mM, Triton X-100 of 0.03% by weight and a phthalic acid buffer solution (pH 5.0) of 100 mM. The second reagent was prepared from bilirubin oxidase (available from Shigma Chemical Co., Ltd. as B1515) of 4 units/ml, p-toluenesulfonic acid 30 mM, EDTA of 1 mM, Triton X-100 of 0.03% by weight and a phosphoric acid buffer solution of 200 mM. The second reagent was adjusted to pH 10.0. The first reagent of 1 ml was pre-heated to 37° C. for 2 minutes, to which 0.05 ml of glucuronide bilirubin obtained in Reference Example 1 was added and reacted for 3 minutes at 37° C. At 37° C., 0.25 ml of the second reagent was added and reacted for 3 minutes. The reaction mixture (a) after adding the first reagent and the reaction mixture (b) after adding the second reagent were analyzed by HPLC and the result is shown in FIG. 1. A reaction mixture (c) was obtained by reacting the glucuronide bilirubin sample with the first reagent which excluded beta-glucuronidase and analyzed by HPLC. The result is also shown in FIG. 1.

In FIG. 1, a peak which was eluted at about 11 minutes is glucuronide bilirubins, and a peak at about 18 minutes is the unconjugated bilirubin. The line (c) in FIG. 1 shows conditions of the sample before reacting with beta-glucuronidase which is a deconjugating enzyme. In FIG. 1, it is clear from comparing (a) with (c) that glucuronide bilirubins were completely converted into the unconjugated bilirubin. It is also clear from comparing (b) with (c) that the unconjugated bilirubin was all oxidized and eliminated by the second reagent.

EXAMPLE 2

Some diluted solutions which contain glucuronide bilirubins purified in Reference Example 1 in various concentration were prepared and a relationship between a glucuronide bilirubin content and absorbance change was examined using the reagent for measuring an amount of all bilirubins prepared in Example 1. The first reagent of 1 ml was pre-heated to 37° C. for 2 minutes, to which 0.05 ml of glucuronide bilirubin solutions having various concentrations was added and reacted for 3 minutes at 37° C. and an absorbance at 460 nm was measured. At 37° C., 0.25 ml of the second reagent was added and reacted for 5 minutes and an absorbance at 460 nm was measured. A linear relationship was obtained between the dilution ratio of the sample and the absorbance change.

EXAMPLE 3

This example shows effects of additives in a sample on the measurement.

The additives, i.e. human albumin (available from Shigma Chemical Co., Ltd. as A 3782), salicylic acid, EDTA and hemoglobin, were respectively added to the glucuronide bilirubin solution purified in Reference Example 1 in an amount shown in Table 1 and a quantitative determination was carried out as generally described in Example 2. The results are described in Table 1. The unconjugated bilirubin of 5 mg/dl in 100 mM Tris-hydrochloric acid buffer (pH 8.0) was used as a standard material.

TABLE 1

| Additive (mg/dl) | Measured value of all bilirubins (mg/dl) |
|---|---|
| Nothing | 10.5 |
| Human albumin | |
| 2 | 10.5 |
| 5 | 10.5 |
| 10 | 10.4 |
| Salicylic acid | |
| 5 | 10.5 |
| 10 | 10.6 |
| EDTA | |
| 50 | 10.5 |
| 500 | 10.6 |
| Hemoglobin | |
| 300 | 10.6 |
| 600 | 10.5 |

As apparent from Table 1, the determination of all bilirubins is not affected at all by the additives. In conventional methods, the effects of such chemical materials present in a sample are very troublesome on the measured value of bilirubins, but the present invention has no such problems.

EXAMPLES 4 AND 5 AND COMPARATIVE EXAMPLES 1 TO 3

The unconjugated bilirubin (available from Daiichi Pure Chemical Co., Ltd.) and ditaurobilirubin, i.e. one of conjugated bilirubins (available from Porphirin Products Inc.) were dissolved in 100 mM of a Tris-hydrochloric acid buffer (pH 8.0) to form solutions of 59 ml/dl and 80 mg/dl, respectively. Further, human albumin was dissolved in 100 mM of a Tris-hydrochloric acid buffer (pH 7.0) to form another solution of 67.0 g/l. The following six samples were prepared from the above three solutions: Sample a only contains the unconjugated bilirubin, sample b only contains ditaurobilirubin, sample c contains the unconjugated bilirubin and ditaurobilirubin, sample d does the unconjugated bilirubin and albumin, sample e does ditaurobilirubin and albumin and sample f does the unconjugated bilirubin, ditaurobilirubin and albumin. In the above samples, ditaurobilirubin was present in an amount of 20 mg/dl, the unconjugated bilirubin in an amount of 20 mg/dl and albumin in an amount of 26.8 mg/dl.

A reagent A which contained 60 mM of a phthalic acid buffer (pH 5.0), 1 units/ml of bilirubin oxidase (available from Shigma Chemical Co., Ltd. as B1515), 0.1 mM of copper sulfate, 0.03% of Triton X-100 (available from Nakarai Chemical Co., Ltd.), 5 mM of p-toluenesulfonic acid and 15 mM of sodium fluoride was prepared for Example 4. For Comparative Example 1, a reagent B was prepared by removing copper sulfate from the reagent A. For Comparative Example 2, a reagent C was prepared by removing Triton X-100 from the reagent A. For Example 5, a reagent D was prepared as generally described in the reagent A with the exception that 0.5 units/ml of glucose oxidase (available from Toyobo Co., Ltd.) and 10 mM of glucose were added instead of bilirubin oxidase. A reagent E for a quantitative determination which contained 100 mM of a citric acid-phosphoric acid buffer (pH 4.0) and 0.1 units/ml of bilirubin oxidase was also prepared as the Example of Japanese Patent Publication (examined) 44000/1986. One ml of each reagent was heated to 37° C. for 2 minutes, to which 0.05 ml of the sample was added and reacted at 37° C. After 5 minutes, a change in absorbance at 460 nm was measured. The results are shown in Table 2.

TABLE 2

| Sample | Absorbance change | | | | |
|---|---|---|---|---|---|
| | A | B | C | D | E |
| a | 0 | 0.23 | 0.19 | 0 | 0.1 |
| b | 0.41 | 0.41 | 0.41 | 0.41 | 0.41 |
| c | 0.41 | 0.65 | 0.60 | 0.41 | 0.41 |
| d | 0 | 0.18 | 0.15 | 0 | 0.05 |
| e | 0.42 | 0.41 | 0.41 | 0.41 | 0.41 |
| f | 0.41 | 0.60 | 0.56 | 0.41 | 0.46 |

As is apparent from the above results, the reagents A and D only reacted with the samples which contain ditaurobilirubin to make an absorbance change, but did not react with the unconjugated bilirubin so that no absorbance change was seen. It is also found that the reagents B, C and E reacted with both the unconjugated bilirubin and ditaurobilirubin. The reagents A and D are superior to the reagent E in fractionating ability and therefore improve measuring inaccuracy. Accordingly, the reagent of the present invention precisely separates bilirubins.

EXAMPLE 6

A reagent for measuring an amount of the unconjugated bilirubin was prepared as follow.

The first reagent was prepared from 0.1 mM of copper sulfate, 0.03% of Triton X-100, 5 mM of p-toluenesulfonic acid, 60 mM of phthalic acid buffer (pH 5.0), 15 mM of sodium fluoride and 1 unit/ml of bilirubin oxidase. The second reagent was prepared from 0.03% of Triton X-100, 20 mM of p-toluenesulfonic acid, 6 mM of EDTA, 200 mM of a phosphoric acid buffer and 10 units/ml of bilirubin oxidase. The second reagent was adjusted to pH 10.0. Also, a standard sample which contained 20 mg/dl of the unconjugated bilirubin, 10 mg/dl of ditaurobilirubin and 26.8 g/l of human albumin was prepared and several diluted standard samples were prepared too.

Figure 2:
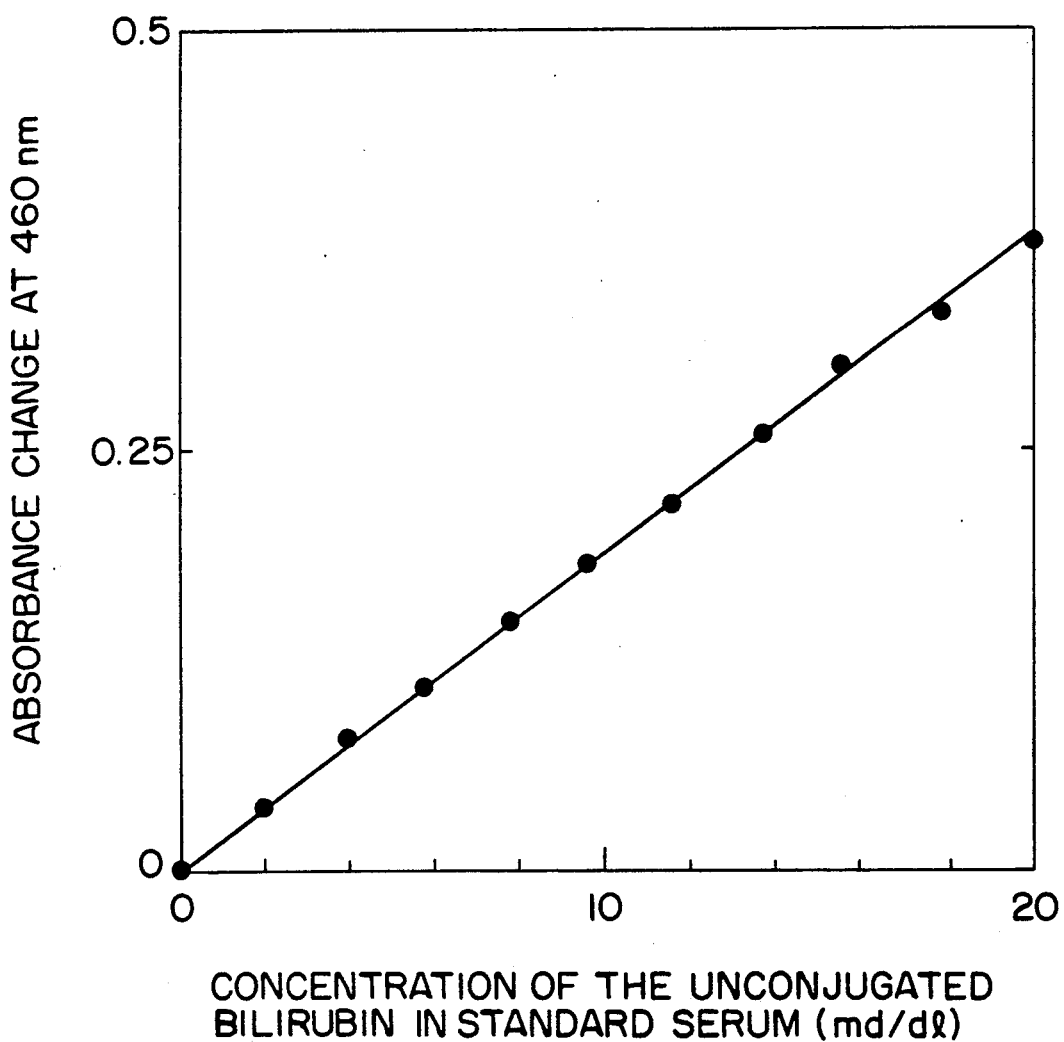
FIG. 2 is a relationship between absorbance change and amount of the unconjugated bilirubin of Example 7.

The first reagent of 1 ml was pre-heated to 37° C. for 2 minutes, to which 0.05 ml of the standard sample having various concentration was added and reacted for 3 minutes at 37° C. An absorbance change at 460 nm was measured. At 37° C., 0.25 ml of the second reagent was added and reacted for 3 minutes, and then an absorbance change at 460 nm was measured. A relationship between the unconjugated bilirubin content and absorbance change was examined and shown in FIG. 2. It has been found from FIG. 2 that a linear relationship is obtainable between the unconjugated bilirubin content and the absorbance change.

EXAMPLE 7

A sample which contained glucuronide bilirubins purified in Reference Example 1 and the unconjugated bilirubin was prepared. The reaction mixture (a) after adding the first reagent and the reaction mixture (b) after adding the second reagent were analyzed by HPLC and the result is shown in FIG. 3. A reaction mixture (c) was obtained by reacting the glucuronide bilirubin sample with the first reagent which excluded bilirubin oxidase and copper sulfate and analyzed by HPLC. The result is also shown in FIG. 3. In FIG. 3, a peak which was eluted at about 11 minutes is glucuronide bilirubins, and a peak at about 18 minutes is the unconjugated bilirubin.

FIG. 3 shows that the first reagent for measuring the unconjugated bilirubins can oxidize and eliminate only the conjugated bilirubins and the remaining unconjugated bilirubin can be quantitatively determined by the addition of the second reagent.

EXAMPLE 8

A standard material A which contained 10 mg/dl of the unconjugated bilirubin, 10 mg/dl of ditaurobilirubin and 26.8 g/l of human albumin was prepared. A sample A was also prepared by mixing 10 ml of a 10 mg/dl unconjugated bilirubin with 1 ml of glucuronide bilirubin sample of Reference Example 1.

The standard material was reacted with the reagent for all bilirubins of Example 1 and the resultant absorbance change was measured. Separately, the sample A was reacted with the reagent for all bilirubins and an absorbance change was measured. An amount of conjugated bilirubins, unconjugated bilirubin and all bilirubins in the sample A was obtained from the absorbance changes and the results are shown in Table 3.

COMPARATIVE EXAMPLE 4

The sample A and standard material A of Example 8 were analyzed by the HPLC method of Reference Example 1. An amount of the unconjugated bilirubin in the sample A was calculated from a proportion of a peak area of the unconjugated bilirubin in the sample A and a peak area of the unconjugated bilirubin in the standard material A. Also, an amount of conjugated bilirubins in the sample A was calculated from the proportion of a peak area of the glucuronide bilirubins in the sample A and a peak area of ditaurobilirubin of the standard material A. The results are shown in Table 3.

TABLE 3

| Analysis | Measured value (mg/dl) | | |
|---|---|---|---|
| method | All bilirubins | Conjugated one | Unconjugate one |
| Present invention | 12.6 | 7.45 | 5.15 |
| HPLC | 12.66 | 7.52 | 5.15 |

In Comparative Example 4, an amount of all bilirubins and the conjugated bilirubins is converted into an amount of the unconjugated bilirubin, provided that glucuronide bilirubins is considered to diglucuronide bilirubin and then calculated from the molecular weight of ditaurobilirubin and the molecular weight of the unconjugated bilirubin.

It has been found from Table 3 that the results from the reagents of the present invention are very close to those from the HPLC method. Especially, the amount of the unconjugated bilirubin is identical in both methods and it is therefore found that the reagents of the present invention has superior in fractionating abilities.

According to the present invention, a quantitative determination of various bilirubins can be carried out precisely by a simple process without influence by the presence of albumin and other chemicals in a specimen. In the present invention, the unconjugated bilirubin which can be easily available is used as a sole standard material and therefore solves the problems of conventional methods, such as inaccuracy and the like. Also, since the present invention uses an enzyme under good conditions for the enzymatic reaction, the performance of the reagent is enhanced. The reagents and methods of the present invention have many advantages, particularly in clinical examinations.

What is claimed is:

1. A process for measuring the amount of all bilirubins in a specimen, comprising:
    deconjugating conjugated bilirubins in the specimen with a reagent comprising an enzyme capable of deconjugation of conjugated bilirubins to form unconjugated bilirubin, and
    determining the amount of unconjugated bilirubin in the specimen.

2. The process according to claim 1 wherein the amount of unconjugated bilirubin is directly determined by a HPLC method.

3. The process according to claim 1 wherein the amount of unconjugated bilirubin is determined from an absorbance change when unconjugated bilirubin is treated with an oxidizing reagent or diazo reagent.

4. A reagent for measuring the amount of all bilirubins in a specimen comprising:
    an enzyme capable of deconjugation of conjugated bilirubin to form unconjugated bilirubin, and
    an oxidizing agent capable of oxidizing bilirubins or a diazo reagent.

5. The reagent according to claim 4 being constituted from two reagents, of which a first reagent comprises the enzyme capable of deconjugation and a second reagent comprises the oxidizing agent capable of oxidizing bilirubins or a diazo reagent.

6. The reagent according to claim 5 wherein said first reagent comprises beta-glucuronidase derived from bovine liver in a concentration of 0.05 to 10 units/ml, p-toluenesulfonic acid in a concentration of 5 to 75 mM, ethylenediaminetetraacetic acid in a concentration of 0.01 to 20 mM and a succinic acid-sodium hydroxide buffer of pH 4 to 6 in a concentration of 20 to 500 mM, and said second reagent contains bilirubin oxidase in a concentration of 0.05 to 10 units/ml, p-toluenesulfonic acid in a concentration of 10 to 50 mM, ethylenediaminetetraacetic acid in a concentration of 0.05 to 50 mM and a phosphoric acid buffer solution of pH 5 to 8 in a concentration of 20 to 500 mM.

7. The reagent according to claim 4 wherein said enzyme capable of deconjugation is sugar ester hydrolase, sulfatase or a mixture thereof.

8. The reagent according to claim 4 wherein said enzyme is employed in a concentration of 0.01 to 100 units/ml.

9. The reagent according to claim 4 which includes an oxidizing agent capable of oxidizing bilirubin and wherein said oxidizing agent capable of oxidizing bilirubins is an enzyme capable of oxidizing bilirubins, an oxidase for producing hydrogen peroxide, a transition metal ion capable of oxidizing bilirubins or a peroxide.

10. The reagent according to claim 4 which includes an oxidizing agent capable of oxidizing bilirubin and wherein said oxidizing agent capable of oxidizing bilirubins is bilirubin oxidase, laccase, glucose oxidase, copper sulfate, copper chloride, ferric sulfate, potassium persulfate or sodium perbenzoate.

11. The reagent according to claim 4 which includes a diazo reagent and wherein said diazo reagent is a hydrochloric acid mixture of sulfanilic acid and nitrous acid, or a mixture of 2,4-dichloroaniline and sulfanilic acid.

12. The reagent according to claim 4 which includes a diazo reagent and wherein said diazo reagent is present in the reagent in a concentration of 0.05 to 5 mM.

13. The reagent according to claim 4 further comprising a reaction promoter, a surfactant, a buffer, a chelating agent, fillers and salts.

14. The reagent according to claim 4 which includes an oxidizing agent capable of oxidizing bilirubin and wherein said oxidizing agent is selected from the group consisting of an enzyme in a concentration of 0.01 to 30 units/ml, a peroxide in a concentration of 0.01 to 50 mM, and a transition metal ion in a concentration of 0.01 to 5 mM.

15. A process for measuring the amount of unconjugated bilirubin in a specimen, comprising:
    oxidizing and eliminating conjugated bilirubins in the specimen with an oxidizing agent capable of oxidizing bilirubins, in the presence of a metal ion forming a complex with bilirubins and a surfactant at pH 6.5 or less, and
    determining the amount of unconjugated bilirubin in the specimen.

16. The process according to claim 15 wherein the amount of unconjugated bilirubin is directly determined by a HPLC method.

17. The process according to claim 15 wherein the amount of unconjugated bilirubin is determined from an absorbance change when unconjugated bilirubin is treated with an oxidizing reagent or diazo reagent.

18. A reagent for measuring the amount of unconjugated bilirubin in a specimen, comprising:
a first reagent comprising an oxidizing agent capable of oxidizing bilirubins, a metal ion forming a complex with bilirubins, a surfactant and a buffer solution of pH 6.5 or less, and
a second reagent comprising at least one component selected from the group consisting of a chelating agent, a buffer solution of pH 6.5 or more and a surfactant.

19. The reagent according to claim 18 wherein said oxidizing agent capable of oxidizing bilirubins is an enzyme capable of oxidizing bilirubins, an oxidase for producing hydrogen peroxide, a transition metal ion capable of oxidizing bilirubins or a peroxide.

20. The reagent according to claim 18 wherein said oxidizing agent capable of oxidizing bilirubins is bilirubin oxidase, laccase, glucose oxidase, copper sulfate, copper chloride, ferric sulfate, potassium persulfate or sodium perbenzoate.

21. The reagent according to claim 18 wherein said metal ion forming a complex with bilirubins is copper ion, iron ion or manganese ion.

22. The reagent according to claim 18 wherein said metal ion forming a complex with bilirubins is present in a concentration of 0.01 to 10 mM.

23. The reagent according to claim 18 wherein said buffer of pH 6.5 or less is a phthalic acid—sodium hydroxide buffer, a succinic acid—sodium hydroxide buffer or a 3,3-dimethylglutaric acid buffer.

24. The reagent according to claim 18 wherein said buffer solution of pH 6.5 or less is present in a concentration of 20 to 200 mM.

25. The reagent according to claim 18 wherein said second reagent includes said buffer of pH 6.5 or more which is a phosphoric acid buffer, a tris hydrochloric acid buffer or a glycine—sodium hydroxide buffer.

26. The reagent according to claim 18 wherein said first reagent comprises 20 to 500 mM of a pH 4.7 to 6.0 buffer solution, 0.025 to 1% of a surfactant, 0.01 to 10 mM of copper sulfate, 0.05 to 20 units/ml of bilirubin oxidase and 5 to 50 mM of sodium fluoride, and said second reagent comprises a pH 5.0 to 7.0 phosphoric acid buffer solution and 0.1 to 50 mM of ethylenediaminetetraacetic acid.

* * * * *